United States Patent [19]

Pratt et al.

[11] Patent Number: 4,636,219

[45] Date of Patent: Jan. 13, 1987

[54] PROSTHESIS DEVICE FABRICATION

[75] Inventors: Clyde R. Pratt, Somis; Roger G. Carignan; Charles M. Raggio, both of Camarillo; Chuck P. Woznick, Oxnard, all of Calif.

[73] Assignee: Techmedica, Inc., Camarillo, Calif.

[21] Appl. No.: 804,927

[22] Filed: Dec. 5, 1985

[51] Int. Cl.$^4$ .............................................. A61F 1/24
[52] U.S. Cl. ...................................... 623/22; 623/18; 228/193
[58] Field of Search ...................... 623/16, 18, 20, 22, 623/23; 228/193, 194, 195

[56] References Cited

U.S. PATENT DOCUMENTS 4,088,258  5/1978  Regalbuto .......................... 228/193
4,570,271  2/1986  Sump ................................. 228/193

OTHER PUBLICATIONS

*Journal of Biochemical Materials Research*, vol. 18, pp. 497-512, (1984) by Cook et al.

Primary Examiner—M. Jordan
Attorney, Agent, or Firm—Cislo, O'Reilly & Thomas

[57] ABSTRACT

A process is disclosed for fabricating a biocompatible mesh screen structure for bonding to a prosthetic substrate. The process comprises providing from four to eight layers of a mesh comprising a titanium alloy and subjecting the layered structure to a temperature below the beta-transformation temperature of the alloy and a pressure of about 1300 to 1500 psi. The heating and pressing are carried out in a furnace maintained at a temperature of about 1600° to 1725° F., which is evacuated to a vacuum of less than about $10^{-4}$ torr. The process of the invention provides a product retaining the strength of the alloy and having a well-characterized pore structure. Further, the layered mesh composite may be bonded to a thin substrate and readily formed into complex shapes.

16 Claims, 5 Drawing Figures

PROSTHESIS DEVICE FABRICATION

BACKGROUND OF THE INVENTION

This invention relates to prosthetic devices for replacement, reconstruction and attachment in the skeletal system of humans and animals, and, more particularly, to a process for fabricating a titanium alloy mesh bone in-growth surface for use in such devices.

Prosthetic devices are used to partially or completely replace joints or bone segments in the skeletal structure of humans or animals. One of the major problems involved in the use of prosthetic devices is the attachment of the prosthetic implant to the adjacent bone. There are four principle methods of which the device can be attached to the bone: (1) force fitting the implant into the medullary canal of the bone; (2) securing the implant in the bone with the aid of screws or pins; (3) bonding the implant by a plastic methyl methacrylic resin which is polymerized "in situ"; and (4) employing in conjunction with the implant a porous material into which the bone may grow.

Each of the first three approaches suffers from one or more advantages, as is well-known. More recently, several variations of the fourth approach have been employed. Examples of these are found in U.S. Pat. Nos. 3,905,777, 3,852,045, 3,886,600, 4,089,071, 4,439,152, 3,906,550 and 4,261,063. While some of these patents do not disclose how the porous material, or mesh, is formed, the patents that do make such disclosure typically teach a sintering process, employing temperatures on the order of 1000° to 1350° C. (1958° to 2462° F.) for titanium and titanium alloys. As is well-known, titanium and titanium alloys (particularly Ti-6Al-4V) are often used in prosthetic devices, due to their biocompatibility. The sintering temperatures employing in fabricating meshes made from such materials results in a degradation of the physical properties of the material. In particular, fatigue values are reduced by more than 50% by the sintering process.

Further, the processes described in the foregoing patents [e.g., U.S. Pat. No. 3,905,777 (layers of perforated foil welded together), U.S. Pat. No. 3,852,045 (sintered particles), or U.S. Pat. No. 3,906,550 (short metal fibers compacted and sintered)] result in meshes that may be considered to be poorly characterized in that the physical properties of strength are not uniform over the surface of the mesh. The non-uniformity of strength, of course, reduces the usefulness of the mesh. Also, such meshes evidence a poorly characterized mesh density, in that the mesh density is variable, with consequent varying degree of bone ingrowth and penetration. The non-uniform bone penetration also reduces the usefulness of the mesh.

Many of the known bone in-growth surface coatings do not readily permit fabrication of custom prostheses. Rather, custom prostheses, if at all possible, are either expensive or take a long time to make by virtue of the necessity of creating special fixturing and jigging.

OBJECTS AND SUMMARY OF THE INVENTION

Accordingly, it is an object of this invention to provide a process for fabricating a biocompatible mesh screen structure having a high degree of strength.

It is another object of this invention to provide a process for fabricating a biocompatible mesh screen structure having substantially uniform strength across the surface of the mesh.

It is yet another object of this invention to provide a process for fabricating a biocompatible mesh screen structure having a substantially uniform pore size so as to promote substantially uniform bone penetration into the mesh.

It is still another object of this invention to provide a process for bonding the mesh to a substrate that may be contoured to a specific geometry for use in a custom prosthesis.

It is a still further object of this invention to create a mesh structure which has inherent strength and which can be formed through a process such as creep forming, into final use/shapes such as hemispherical shells for actabular cups.

These and further objects of the invention will become apparent from the hereinafter following commentary taken in conjunction with the drawing.

In accordance with the invention, a process is provided for fabricating a biocompatible mesh screen structure for bonding to a prosthetic substrate. The process comprises providing from four to eight layers of a mesh comprising a titanium alloy and subjecting the layered structure to a temperature below the beta-transformation temperature of the alloy and a pressure of about 1300 to 1500 psi. The heating and pressing are carried out in a furnace heated to a temperature of about 1600° to 1725° F. and evacuated to a vacuum of less than about $10^{-4}$ torr.

The mesh screen structure fabricated in accordance with the invention employs mesh screens of substantially uniform pore size that is retained during processing. Use of a substantially uniform pressure across the mesh screen structure during processing ensures a much stronger mesh than heretofore available.

The mesh screen structure so produced may be bonded to a thin substrate, which may be formed into a particular shape for custom application, if desired. The vacuum heating process described above may be employed for such bonding to the substrate or other suitable bonding process may be employed.

DESCRIPTION OF THE BEST EMBODIMENTS CONTEMPLATED

Figure 1:
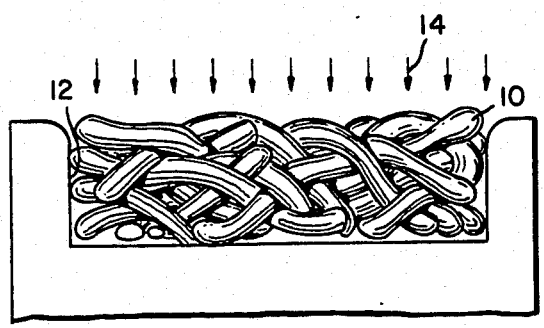
FIG. 1 depicts a prior art approach, involving diffusion bonding of short, random lengths of wire.
Figure 2A:
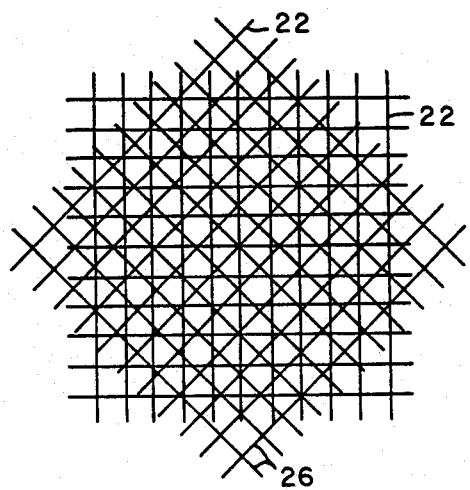
FIG. 2a is a plan view of the stacking of two layers of mesh screen, showing the preferred orientation of one layer with respect to the next layer.

Referring to the drawing, wherein like numerals of reference designate like elements throughout, FIG. 1 depicts the prior art fabrication of a porous surfaced material for surgical implantation. In this prior art process, a number of chopped fibers 10 are placed in a cavity 12 and subjected to heat and pressure, the pressure being denoted by arrows 14. The temperature is described as comparatively low, about 50 to 60% of the melting point of the alloy (Ti-6Al-4V). The process, considered to be proprietary, is said to help retain the integrity of the microstructure. This is in contrast to bonding by sintering, which is performed at temperatures about 90 to 95% of the melting point of the alloy.

Nevertheless, the use of short, chopped fibers provides a product having a poorly characterized pore structure, resulting in varying density across the pressure pattern. This means that bone will grow into the mesh with varying rates and varying amounts of penetration. This also means that the chopped fiber will bond to adjacent fibers with varying degrees of success.

In accordance with the invention, a process is provided for fabricating a biocompatible mesh screen structure 20 for bonding to a prosthetic substrate. The process, termed "vacuum diffusion bonding", employs a temperature below the beta-transformation temperature of the alloy. Heating above the beta-transformation temperature of titanium alloys results in severe reduction in fatigue values, while heating below this temperature has been found to retain the high strength properties of the alloy.

The beta-transformation temperature is that temperature at which the alpha phase of the alloy transforms to the beta phase. In the case of titanium metal, the alpha phase is a hexagonal close packed structure, with a=2.95 KX and b=4.683 KX. The beta-transformation occurs at 885° C. (1625° F.) and transforms the crystal lattice into a body centered cubic structure, with a=3.306 KX. The beta-transformation temperature for the alloy Ti-6Al-4V occurs at 1800° to 1825° F.

The process of the invention comprises providing from four to eight layers 22 of a mesh comprising a titanium alloy and subjecting the layered structure to a temperature below the beta-transformation temperature of the alloy and a pressure, denoted by arrows 24, of about 1300 to 1500 psi. The heating and pressing are carried out in a furnace heated to about 1600° to 1725° F. and evacuated to a vacuum of less than about $10^{-4}$ torr. The heating and pressing are carried out for a period of time of about 12 to 24 minutes.

The titanium alloy of the invention may comprise any of the biocompatible alloys known in the art. As used herein, the term "titanium alloy" includes titanium metal of the type commonly employed in prosthetic devices. Preferably, the titanium alloy may comprise commercially pure titanium or the alloy known as Ti-6Al-4V.

The layers 22 of mesh 20 comprise wires 26 formed substantially at right angles and having a substantially uniform pore size. Conveniently, wire of 0.010 inch diameter is employed, using a #26 weave, which provides 0.028 inch centers. Other weaves may be employed; use of such other weaves will require adjustment of the wire diameter to obtain a desired mesh structure 20.

Each layer 22 is preferably oriented at 45° with respect to its neighboring layer. The triangular-shaped areas 28 which extend beyond the boundaries of the neighboring layers are considered waste and may be trimmed either prior to processing or subsequent thereto.

In the process of the invention, from four to eight layers 22 are placed in a platten (not shown) which is maintained in a furnace (not shown). The platten gap is held at about 0.070 to 0.075 inch (room temperature, for six layers). The furnace is preheated to a temperature of 1600° to 1725° F., depending on the particular titanium alloy. The platten is brought to the desired temperature in the furnace, preferably about 1600° F. for commercially pure Ti and about 1650° F. for the alloy Ti-6Al-4V, and maintained at that temperature for about 12 to 24 minutes. The pressure of about 1300 to 1500 psi is applied once the materials are at the desired temperature and is released prior to cooling. During the entire process, the furnace is evacuated to a vacuum below about $10^{-4}$ torr, with less than 1 ppm residual impurities, to ensure purity of the furnace atmosphere. Cooling of the structure 20 is accomplished simply by allowing the furnace and platten to cool to room temperature.

The resulting mesh structure 20 has a thickness of about 0.070 to 0.075 inch (for six layers), with an effective pore size ranging from about 15 to 860 micrometers (mean about 235 micrometers). Importantly, no change in the microstructure occurs as a consequence of the processing being carried out at a temperature below the beta-transformation temperature, thereby eliminating adverse effects to mechanical and fatigue resistant properties. Although the pore size varies, it varies consistently and density does not vary substantially.

The same temperature-pressure process described above may be employed in bonding a mesh structure 20 to a substrate (not shown).

The primary benefit of the process of the invention as compared with prior art approaches is that the wire mesh layers are well-characterized. Thus, when they are stacked one upon the other and pressure is applied, the pressure between each wire level and the substrate is even. Therefore, one can be assured that the bonding between each layer and substrate is even and of high quality. This results in a much stronger mesh coating than any of the others presently available.

Thus, in contrast to the random bonding of the prior art, the use of the process of the invention provides discrete, regular bonding points of the mesh structure.

Another benefit of the process of the invention is a well-characterized pore structure. This is to say that the density is even across the mesh surface. This is significant when compared to the prior art product, depicted in FIG. 1.

A further benefit of the process of the invention lies in the fact that the mesh 20 produced may be bonded to a thin substrate (on the order of 0.010 to 0.012 inch). This thin substrate can then be cut or formed and applied to the body of a prosthesis 30, shown in FIG. 3, such as by additional vacuum diffusion bonding, as described above, or by mechanical interfit or by electron beam or by other welding technique. This allows use of the mesh 20 in situations other than mass production; that is, the mesh may be contoured for a specific geometry and then applied to a custom prosthesis. In particular, the mesh composite structure 20 may be formed into complex shapes, such as hemispherical shape or an acetabular cup 40 shown in FIG. 4, by processes such as creep forming.

Figure 3:
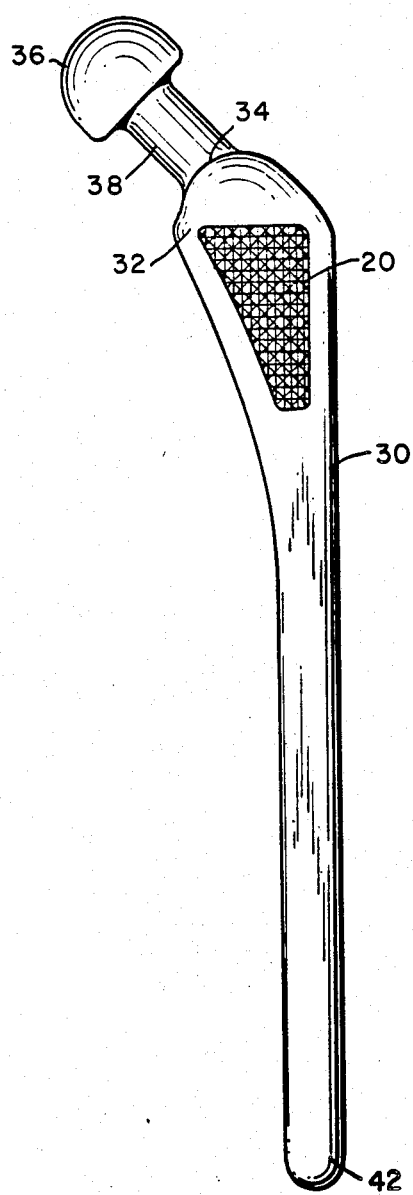
FIG. 3 is a side elevational view of a prosthetic device, employing the mesh screen structure produced by the process of the invention.
Figure 2B:
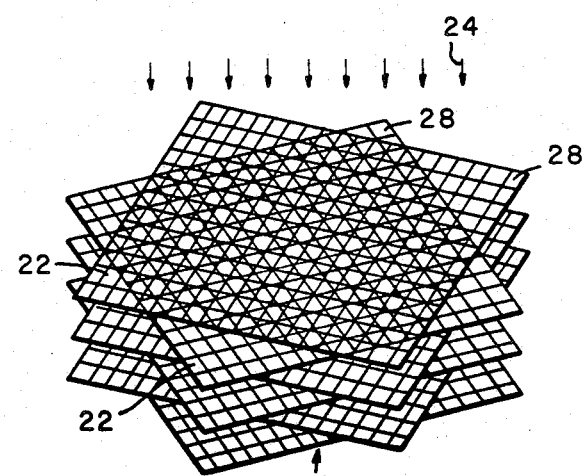
FIG. 2b is a perspective view showing six layers in stacked configuration.
Figure 4:
FIG. 4 is a side elevational view of an acetabular cup, employing the mesh screen structure produced by the process of the invention.

Shown in FIG. 3 is the prosthesis 30, comprising a curved portion 32, to a portion of which is bonded the mesh 20, a rim 34 at the upper end of the curved portion 32, and a spherical head 36 connected to the rim 34 by neck 38. The lower end 42 of the curved portion 32 permits insertion into the medular duct of the femur. The prosthesis 30 is then suitably employed as a femoral pin for hip prosthesis.

Of course, it will be appreciated that the process of the invention may be employed to fabricate prosthetic devices for other areas of the skeletal structure.

Thus, there has been disclosed a process for fabricating a biocompatible mesh screen structure for bonding to a prosthetic substrate. Various modifications and changes will make themselves available to those of ordinary skill in the art, and all such changes and variances not deviating from the spirit and essence of the invention are intended to be covered by the appended claims.

What is claimed is:

1. A process of fabricating a biocompatible mesh screen structure for bonding to a prosthetic substrate, the process comprising:
   (a) providing from four to eight layers of a mesh comprising a titanium alloy; and
   (b) subjecting the layered structure to a processing temperature below the beta-transformation temperature of said alloy and a pre-determined pressure for a pre-selected period of time, the heating and pressing being carried out in a vacuum furnace maintained at a temperature of about 25° to 125° F. above said processing temperature and at a pre-determined vacuum.

2. The process of claim 1 wherein said alloy comprises a member selected from the group consisting of commercially pure titanium and Ti-6Al-4V.

3. The process of claim 2 wherein said processing temperature is at least about 1600° F., said pre-determined pressure ranges from about 1300 to 1500 psi, said pre-selected period of time ranges from about 12 to 24 minutes and said pre-determined vacuum is less than about $10^{-4}$ torr.

4. A process for fabricating a biocompatible mesh screen structure for bonding to a prosthetic substrate, the processing comprising:
   (a) providing from four to eight layers of a mesh comprising a titanium alloy; and
   (b) subjecting the layered structure to a processing temperature below the beta-transformation temperature of said alloy and a pressure of about 1300 to 1500 psi for a period of time of about 12 to 24 min, the heating and pressing being carried out in a furnace maintained at a temperature ranging from about 1600° to 1725° F., depending upon the alloy, said furnace evacuated to provide a vacuum of less than about $10^{-4}$ torr.

5. The process of claim 4 wherein said mesh comprises a member selected from the group consisting of commercially pure titanium and Ti-6Al-4V.

6. The process of claim 5 wherein said processing temperature is about 1600° for commercially pure Ti and about 1650° F. for Ti-6Al-4V.

7. The process of claim 4 wherein the pore size of said mesh ranges from about 15 to 860 micrometers.

8. The process of claim 7 wherein said pore size averages about 235 micrometers.

9. The process of claim 4 wherein said mesh is comprised of wires having a diameter of about 0.01 inch.

10. The process of claim 4 wherein each layer is biased 45° with respect to its neighboring layers.

11. Product produced by the process of claim 4.

12. A process for fabricating a biocompatible mesh screen structure bonded to a prosthetic substrate comprising:
   (a) providing from four to eight layers of a mesh comprising a titanium alloy:
   (b) providing a substrate of a titanium alloy; and
   (c) subjecting the structure to a processing temperature below the beta-transformation temperature of said alloy and a pressure of about 1300 to 1500 psi for a period of time of about 12 to 24 minutes, the heating and pressing being carried out at a furnace maintained at a temperature ranging from about 1600° to 1725° F., said furnace being evacuated to provide a vacuum of less than about $10^{-4}$ torr.

13. The process of claim 12 wherein said titanium alloy comprises a member selected from the group consisting of commercially pure titanium and Ti-6Al-4V.

14. The process of claim 13 wherein said processing temperature is about 1600° F. for commercially pure Ti and about 1650° F. for Ti-6Al-4V.

15. The process of claim 12 wherein said prosthetic substrate comprises a titanium alloy.

16. Product produced by the process of claim 12.

* * * * *